(12) United States Patent
Kitano (10) Patent No.: US 10,499,798 B2
(45) Date of Patent: Dec. 10, 2019

(54) ENDOSCOPE

(71) Applicant: FUJIFILM Corporation, Tokyo (JP)

(72) Inventor: Ryo Kitano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 74 days.

(21) Appl. No.: 15/428,147

(22) Filed: Feb. 8, 2017

(65) Prior Publication Data

US 2017/0251914 A1    Sep. 7, 2017

(30) Foreign Application Priority Data

Mar. 3, 2016 (JP) .................................. 2016-040838

(51) Int. Cl.
*A61B 1/05* (2006.01)
*A61B 1/00* (2006.01)
(Continued)

(52) U.S. Cl.
CPC .......... *A61B 1/051* (2013.01); *A61B 1/00018* (2013.01); *A61B 1/00114* (2013.01);
(Continued)

(58) Field of Classification Search
CPC ..... A61B 1/00114; A61B 1/018; A61B 1/051; A61B 1/128; A61B 1/00018;
(Continued)

(56) References Cited

U.S. PATENT DOCUMENTS

| | | |
|---|---|---|
| 4,831,456 A | 5/1989 | Takamura |
| 6,567,115 B1 | 5/2003 | Miyashita et al. |

(Continued)

FOREIGN PATENT DOCUMENTS

| | | |
|---|---|---|
| JP | S63272180 | 11/1988 |
| JP | H1099267 | 4/1998 |

(Continued)

OTHER PUBLICATIONS

"Search Reposrt of European Counterpart Application," dated Jan. 4, 2018, p. 1-p. 13.

(Continued)

*Primary Examiner* — Anner N Holder
(74) *Attorney, Agent, or Firm* — JCIPRNET (57) ABSTRACT

An endoscope has an imaging unit at a tip portion of an insertion unit to be inserted into a body cavity, and the imaging unit includes: a solid-state imaging device which is disposed in such a manner that a photodetecting surface thereof crosses a longitudinal direction of the insertion unit and which performs photoelectric conversion on an optical image formed on the photodetecting surface; a circuit board having a connection surface which is opposed to a surface, opposite to the photodetecting surface and formed with connection terminals, of the solid-state imaging device and which serves for electrical connection to the connection terminals of the solid-state imaging device, wherein the circuit board is a rigid board that is L-shaped as defined herein; and a first leg and a second leg that constitute the L-shaped circuit board and are perpendicular to each other are provided as defined herein.

10 Claims, 10 Drawing Sheets

(51) Int. Cl.
- *A61B 1/018* (2006.01)
- *A61B 1/12* (2006.01)
- *H04N 5/225* (2006.01)
- *G02B 23/24* (2006.01)

(52) U.S. Cl.
CPC .............. *A61B 1/018* (2013.01); *A61B 1/128* (2013.01); *G02B 23/2484* (2013.01); *H04N 5/2257* (2013.01); *G02B 23/2469* (2013.01); *H04N 5/2253* (2013.01); *H04N 5/2254* (2013.01); *H04N 2005/2255* (2013.01)

(58) Field of Classification Search
CPC ............ G02B 23/2469; G02B 23/2484; H04N 2005/2255; H04N 5/2253; H04N 5/2254; H04N 5/2257
See application file for complete search history.

(56) References Cited

U.S. PATENT DOCUMENTS

| | | | |
|---|---|---|---|
| 9,226,646 | B2 | 1/2016 | Kubo et al. |
| 2008/0255416 | A1 | 10/2008 | Gilboa |
| 2011/0172492 | A1* | 7/2011 | Erikawa ............... A61B 1/0638 600/178 |
| 2011/0245600 | A1 | 10/2011 | Ishii et al. |
| 2011/0249106 | A1* | 10/2011 | Makino ................ H04N 5/2254 348/76 |
| 2013/0064530 | A1* | 3/2013 | Sekido ............... A61B 1/00124 396/17 |
| 2014/0320621 | A1* | 10/2014 | Sonnenschein ........ A61B 1/012 348/76 |
| 2016/0037029 | A1* | 2/2016 | Igarashi ............. G02B 23/2476 348/65 |
| 2016/0119528 | A1* | 4/2016 | Adachi .................... A61B 1/04 348/68 |
| 2017/0332894 | A1* | 11/2017 | Fujii ..................... A61B 1/127 |

FOREIGN PATENT DOCUMENTS

| | | |
|---|---|---|
| JP | 2000199863 | 7/2000 |
| JP | 2008532574 | 8/2008 |
| JP | 2008253451 | 10/2008 |
| JP | 2014027419 | 2/2014 |
| JP | 2014027431 | 2/2014 |
| JP | 2015-062555 | 4/2015 |
| JP | 2016036558 | 3/2016 |
| WO | 2014171275 | 10/2014 |

OTHER PUBLICATIONS

"Search Report of European Counterpart Application," dated Oct. 23, 2017, p. 1-p. 13.

"Office Action of Japan Counterpart Application," dated Dec. 4, 2018, with English translation thereof, p. 1-p. 11.

"Office Action of Japan Counterpart Application," dated May 21, 2019, with English translation thereof, p. 1-p. 9.

* cited by examiner

ENDOSCOPE

CROSS-REFERENCE TO RELATED APPLICATIONS

This application claims the benefit of Japanese Patent Application JP 2016-040838, filed Mar. 3, 2016, the entire content of which is hereby incorporated by reference, the same as if set forth at length.

FIELD OF THE INVENTION

The present invention relates to an endoscope.

BACKGROUND OF THE INVENTION

In general, an imaging unit that is installed in a tip portion of an insertion unit of an endoscope is equipped with an image sensor and a circuit board on which the image sensor is mounted. And plural electric wires inserted through the insertion unit are connected to the circuit board.

JP-A-2015-62555 discloses an imaging unit in which a circuit board is disposed behind an image sensor and electric wires are soldered to plural surfaces of the circuit board.

SUMMARY OF THE INVENTION

In the imaging unit disclosed in JP-A-2015-62555, since the electric wires are connected to the plural surfaces of the circuit board, a process of connecting the electric wires to the individual surfaces of the circuit board while changing the orientation of the circuit board is complex. Furthermore, to prevent a phenomenon that an electric wire that is already soldered to one board surface is disconnected due to heat that is generated in soldering another electric wire to another board surface, a careful temperature control is necessary in which the solder temperature is varied for each board surface when an electric wire is connected to it. This further complicates the process of connecting the electric wires.

The present invention has been made in view of the above circumstances, and an object of the invention is therefore to provide an endoscope that is easy to manufacture and whose insertion unit can be reduced in diameter.

According to an aspect of the invention, there is provided an endoscope having an imaging unit at a tip portion of an insertion unit to be inserted into a body cavity, the imaging unit comprising: a solid-state imaging device which is disposed in such a manner that its photodetecting surface crosses the longitudinal direction of the insertion unit and which performs photoelectric conversion on an optical image formed on the photodetecting surface; a circuit board having a connection surface which is opposed to a surface, opposite to the photodetecting surface and formed with connection terminals, of the solid-state imaging device and which serves for electrical connection to the connection terminals of the solid-state imaging device, wherein: the circuit board is a rigid board that is L-shaped when viewed in its width direction that is perpendicular to the longitudinal direction of the insertion unit; and of a first leg and a second leg that constitute the L-shaped circuit board and are perpendicular to each other, the first leg which is opposed to the solid-state imaging device has the connection surface on the side of the solid-state imaging device and transmission cables are electrically connected to an inner surface of the second leg, the inner surface having a smaller area, than an area of an outer surface of the second leg, in a plane including the longitudinal direction of the insertion unit and the width direction of the circuit board, the outer surface being opposite to the inner surface.

According to the invention, since the transmission cables are connected to the inner surface of the second leg which is one surface of the L-shaped circuit board, the transmission cables can be connected easily to the circuit board of the imaging unit even if the imaging unit is disposed in the small-diameter insertion unit of the endoscope. This makes it possible to provide an endoscope that is easy to manufacture and whose insertion unit can be reduced in diameter.

BRIEF DESCRIPTION OF THE DRAWINGS

FIGS. 8A and 8B illustrate how the solid-state imaging device and the circuit board are connected to each other; FIG. 8A shows a case that a cable connection portion is warped to the side of its inner surface, and FIG. 8B shows a case that the cable connection portion is warped to the side of its outer surface.

FIGS. 9A and 9B illustrate why the manner of arrangement of transmission cables affects the necessary width of the cable connection portion; FIG. 9A shows a case that first cables are disposed outside, and FIG. 9B shows a case that second cables are disposed outside.

DESCRIPTION OF SYMBOLS

1: Endoscope system
2: Endoscope
14: Treatment tool channel
20: Imaging unit
21: Image sensor (solid-state imaging device)
21a: Photodetecting surface
24: Circuit board
25: Land
26: Connection terminal
27: Cable
27L: First cable
27S: Second cable
27b: Shield conductor
28: Case member
30: Sensor connection portion (first leg)
30a: Connection surface
31: Cable connection portion (second leg)

32a: Inner surface
31b: Outer surface

DETAILED DESCRIPTION OF THE INVENTION

Figure 1:
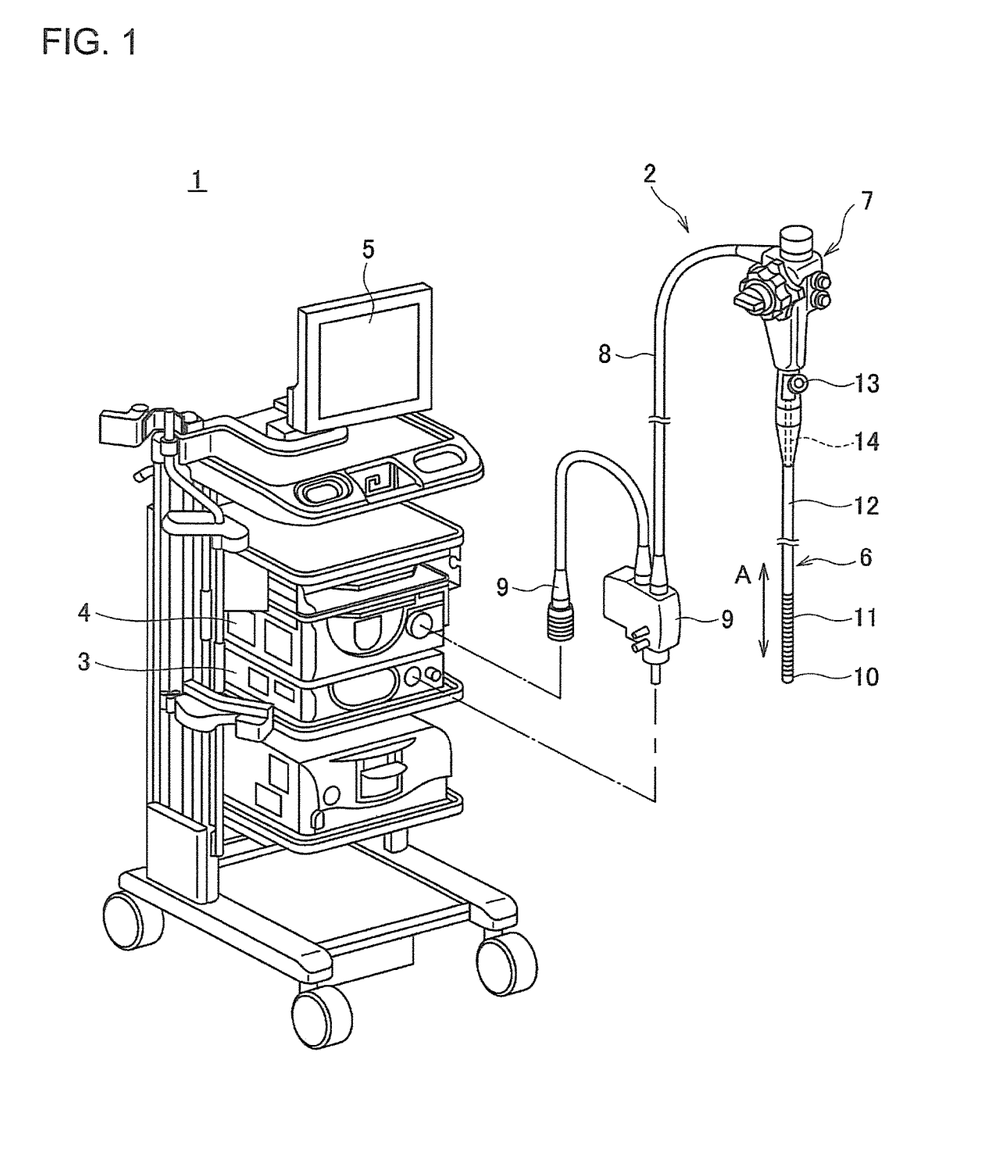
FIG. 1 shows the configuration of an example endoscope system for description of an embodiment of the present invention.

FIG. 1 shows an example endoscope system 1 for description of an embodiment of the present invention. The endoscope system 1 is composed of an endoscope 2, a light source unit 3, and a processor unit 4. The endoscope 2 is equipped with an insertion unit 6 to be inserted into a subject body, a manipulation unit 7 which is continuous with the insertion unit 6, and a universal cord 8 which extends from the manipulation unit 7. The insertion unit 6 is composed of a tip portion 10, a bendable portion 11 which is continuous with the tip portion 10, and a soft portion 12 which links the bendable portion 11 to the manipulation unit 7.

The tip portion 10 is equipped with illumination optical systems for emitting illumination light for illumination of an observation part, an imaging unit and an imaging optical system for shooting the observation part, and other components. The bendable portion 11 is configured so as to be bendable perpendicularly to the longitudinal axis of the insertion unit 6, and is bent by manipulating the manipulation unit 7. The soft portion 12 is configured so as to be relatively flexible, that is, flexible enough to deform so as to conform to the shape of an insertion route for the insertion unit 6.

The manipulation unit 7 is equipped with buttons for making a manipulation for an imaging operation of the imaging unit installed in the tip portion 10, a knob for making a manipulation for bending the bendable portion 11, and other members. The manipulation unit 7 is formed with an insertion inlet 13 through which a treatment tool such as an electric scalpel is to be inserted, and a treatment tool channel 14 through which a treatment tool such as forceps is to be inserted is formed in the insertion unit 6 so as to extend from the insertion inlet 13 to the tip portion 10.

Connectors 9 are provided at an intermediate position and one end of the universal cord 8. The endoscope 2 is connected, via the connector(s) 9, to the light source unit 3 for generating illumination light to be emitted from the illumination optical system provided in the tip portion 10 and the processor unit 4 for processing a video signal acquired by the imaging unit provided in the tip portion 10. The processor unit 4 generates video data of an observation part by processing a received video signal and displays the generated video data on a monitor 5. Furthermore, the processor unit 4 has the generated video data recorded.

Light guides and cables are disposed inside the insertion unit 6, the manipulation unit 7, and the universal cord 8. Illumination light generated by the light source unit 3 is guided by the light guides to the illumination optical systems provided in the tip portion 10, and signals and power are transmitted between the image unit provided in the tip portion 10 and the processor unit 4 by the cables.

FIGS. 2-5 show the configuration of the imaging unit 20 installed in the tip portion 10 of the insertion unit 6. The imaging unit 20 is equipped with an image sensor (solid-state imaging device) 21 such as a CCD (charge-coupled device) image sensor or a CMOS (complementary metal-oxide-semiconductor) image sensor, a lens barrel 22 which houses an imaging optical system for forming a subject image on a photodetecting surface 21a of the image sensor 21, a sensor holder 23 which holds the image sensor 21 and the lens barrel 22, a circuit board 24 on which the image sensor 21 is mounted, and a metal (conductor) case member 28 which covers part of the image sensor 21 and part of the circuit board 24.

The sensor holder 23 holds the lens barrel 22 in such a manner that the lens barrel 22 is movable along the optical axis B (see FIG. 5) of the imaging optical system and the position of the image sensor 21 is thereby adjustable relative to the imaging optical system. The lens barrel 22 is fixed to the sensor holder 23 with, for example, adhesive after the image sensor 21 is positioned with respect to it.

The image sensor 21 is disposed in such a manner that its photodetecting surface 21a crosses the longitudinal direction of the insertion unit 6, and performs photoelectric conversion on an optical image formed on the photodetecting surface 21a. The outer size of the image sensor 21 is smaller than or equal to a 1-mm square when viewed perpendicularly to the photodetecting surface 21a. The back surface of the image sensor 21, that is, its surface opposite to the photodetecting surface 21a, is provided with plural connection terminals 26 for receiving and outputting signals and power.

The circuit board 24 has a sensor connection portion 30 and a cable connection portion 31. The sensor connection portion 30 has a connection surface 30a which is opposed to the surface, opposite to the photodetecting surface 21a and provided with the connection terminals 26, of the image sensor 21 and serves for electric connection to the respective connection terminals 26 of the image sensor 21.

Figure 4:
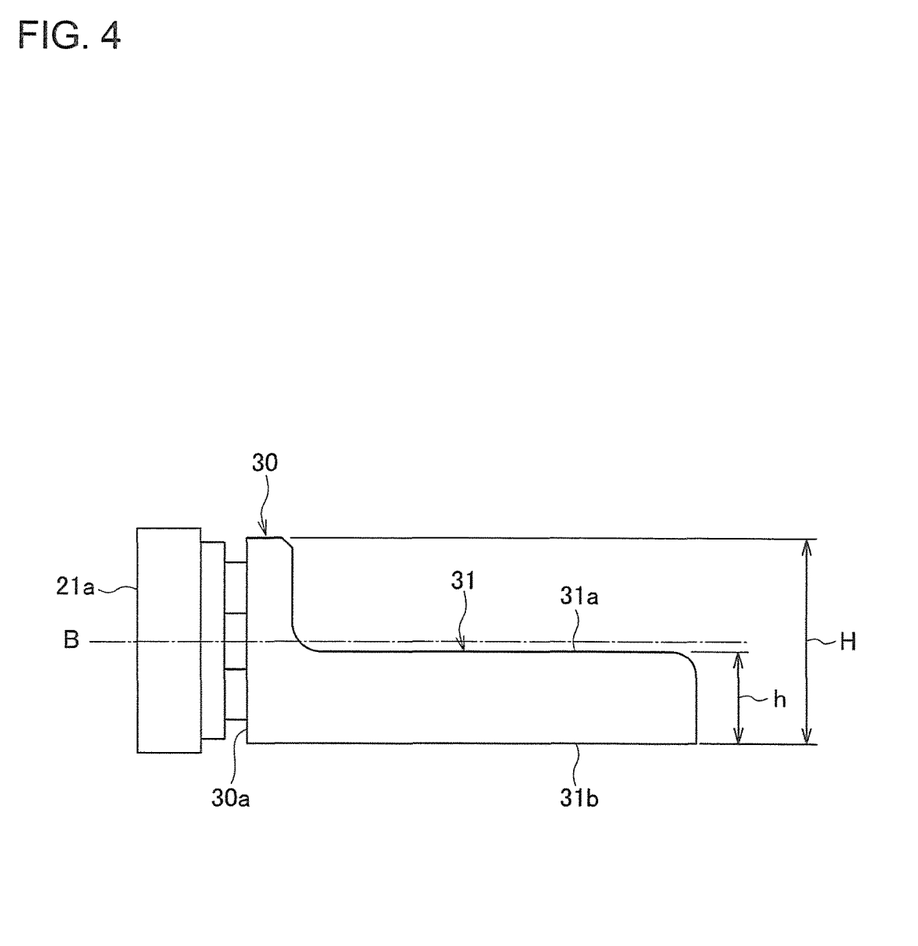
FIG. 4 is a side view illustrating how a solid-state imaging device and a circuit board are connected to each other in the imaging unit of FIG. 2.
Figure 5:
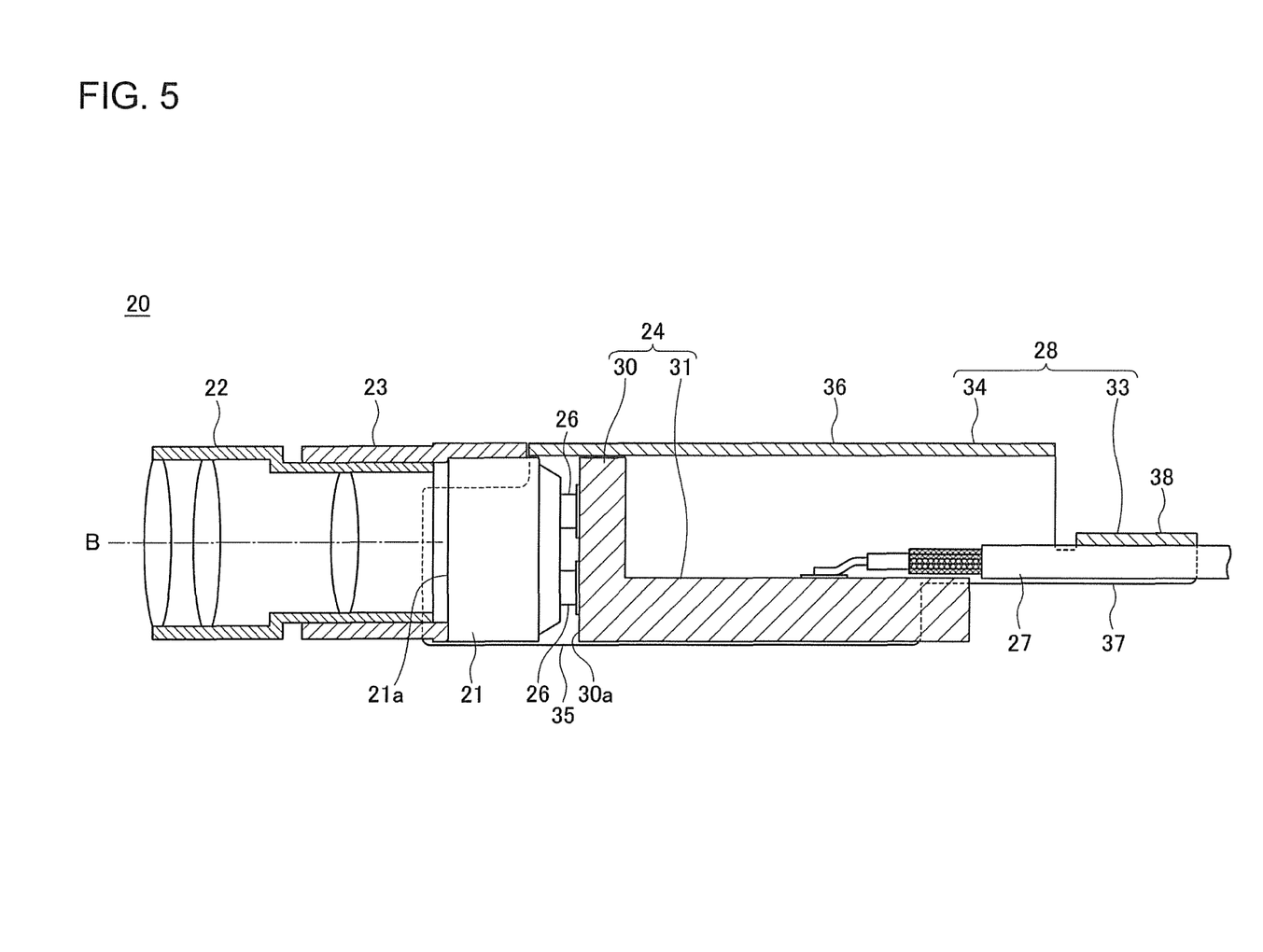
FIG. 5 is a sectional view of the imaging unit of FIG. 2.

The connection surface 30a of the sensor connection portion 30 is formed with plural lands 25. The sensor connection portion 30 is set adjacent to the back surface of the image sensor 21, and the connection terminals 26 formed on the back surface of the image sensor 21 are connected to the respective lands 25 of the sensor connection portion 30 directly, that is, without intervention of electric wires or the like.

The circuit board 24 is a rigid circuit board that is L-shaped when viewed in the width direction (indicated by arrow W in FIG. 3) that is perpendicular to the longitudinal direction of the insertion unit 6. The sensor connection portion 30 and the cable connection portion 31 are approximately perpendicular to each other. More specifically, in the embodiment, one of the two legs constituting the circuit board 24 is the sensor connection portion 30 and the other (second leg) is the cable connection portion 31. The sensor connection portion 30 is set adjacent to the back surface of the image sensor 21 and parallel with its photodetecting surface 21a. The cable connection portion 31 exists behind the image sensor 21 and extends approximately perpendicularly to its photodetecting surface 21a. The thickness of the cable connection portion 31 (i.e., the dimension indicated by arrow h in FIG. 4) is about 0.3 mm.

The circuit board 24 is disposed in such a manner that its outer periphery coincides with the outer periphery of the image sensor 21 when the circuit board 24 and the image sensor 21 are projected onto a plane that is perpendicular to the longitudinal direction of the insertion unit 6. In other words, as shown in FIG. 4, the circuit board 24 is disposed so as to be completely hidden behind the image sensor 21 when viewed from the side of the photodetecting surface 21a of the image sensor 21 in the direction of the optical axis B.

A smaller-area surface, defined in a plane including the longitudinal direction of the insertion unit 6 and the width direction (indicated by arrow W in FIG. 3) of the circuit board 24, of the cable connection portion (second leg) 31, that is, an inner surface 31a, is formed with plural lands 32 which are arranged in line in the width direction W of the circuit board 24. Plural cables 27 (transmission cables) are electrically connected to the respective lands 32. Each cable 27 is a coaxial cable in which a center conductor 27a is surrounded by a shield conductor 27b for electromagnetic shielding. An exposed portion of the center conductor 27a at a tip portion of a terminal portion of each cable 27 is connected to a land 32. The image sensor 21 which is mounted on the circuit board 24 is connected to the processor unit 4 via the circuit board 24 and the plural cables 27.

Figure 3:
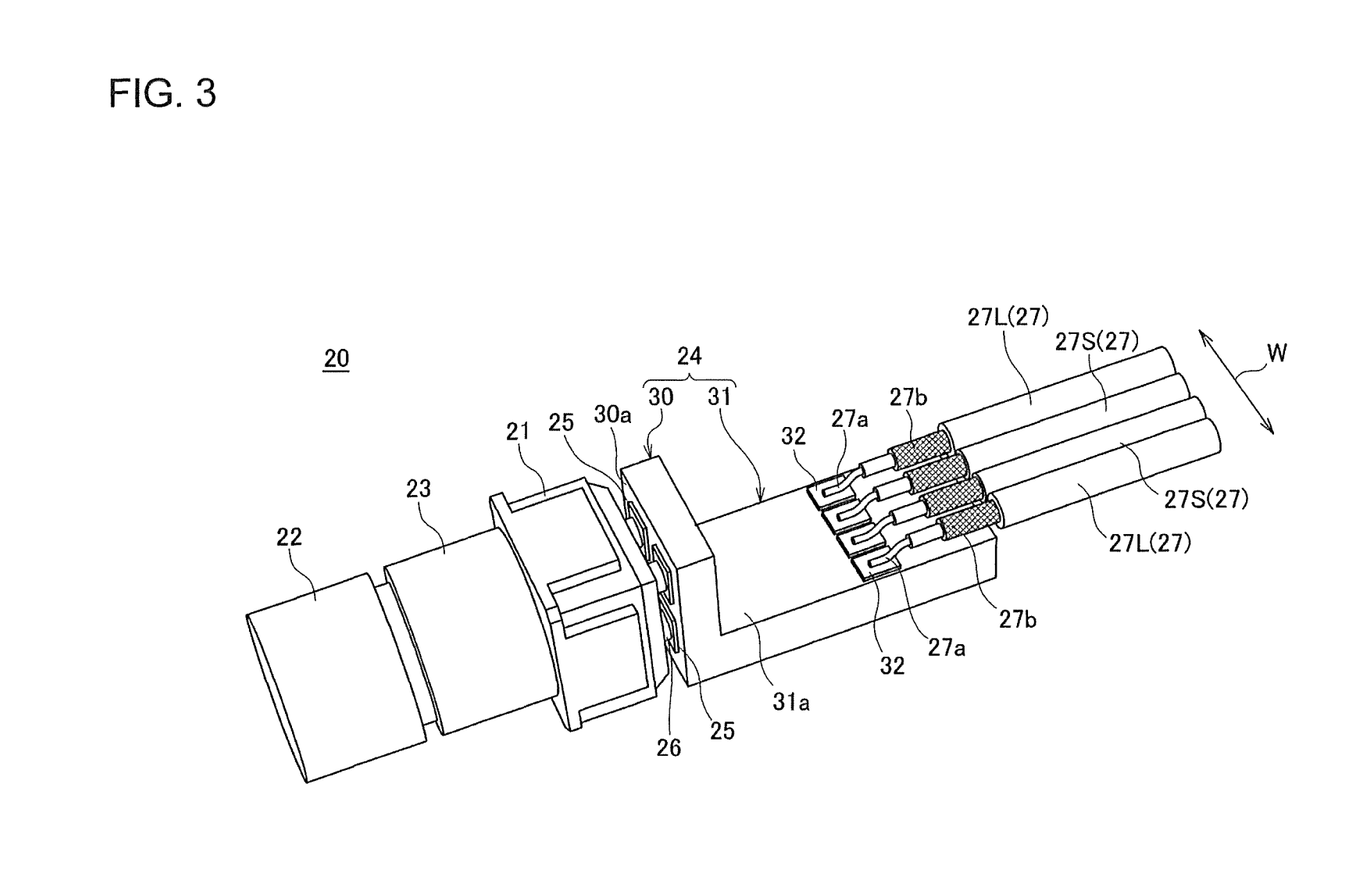
FIG. 3 is a perspective view, as viewed from a different direction than in FIG. 2, of the imaging unit (excluding a case member) installed in the tip portion of the insertion unit of the endoscope shown in FIG. 1.

In the embodiment, the transmission cables which are four cables 27, that is, two first cables 27L which are relatively large in diameter and two second cables 27S which are relatively small in diameter, are connected to the cable connection portion 31. The first cables 27L are about 0.3 mm in diameter and the second cables 27S are about 0.2 mm in diameter. These four cables 27 are disposed on the inner surface 31a of the cable connection portion (second leg) 31 so as to be arranged side by side in the width direction W of the circuit board 24. The first cables 27L are disposed as the outermost cables.

The relatively wide first cables 27L are used as cables for transmitting signals that likely cause problems if distorted in waveform, such as a clock signal cable and an output signal cable. On the other hand, the relatively narrow cables 27S are used as cables for which parameter adjustment is possible, such as a power cable and a ground cable. The first cables 27L are close to the case member 28, and their shield conductors 27b are electrically connected to the case member 28 by silver paste or solder.

Figure 2:
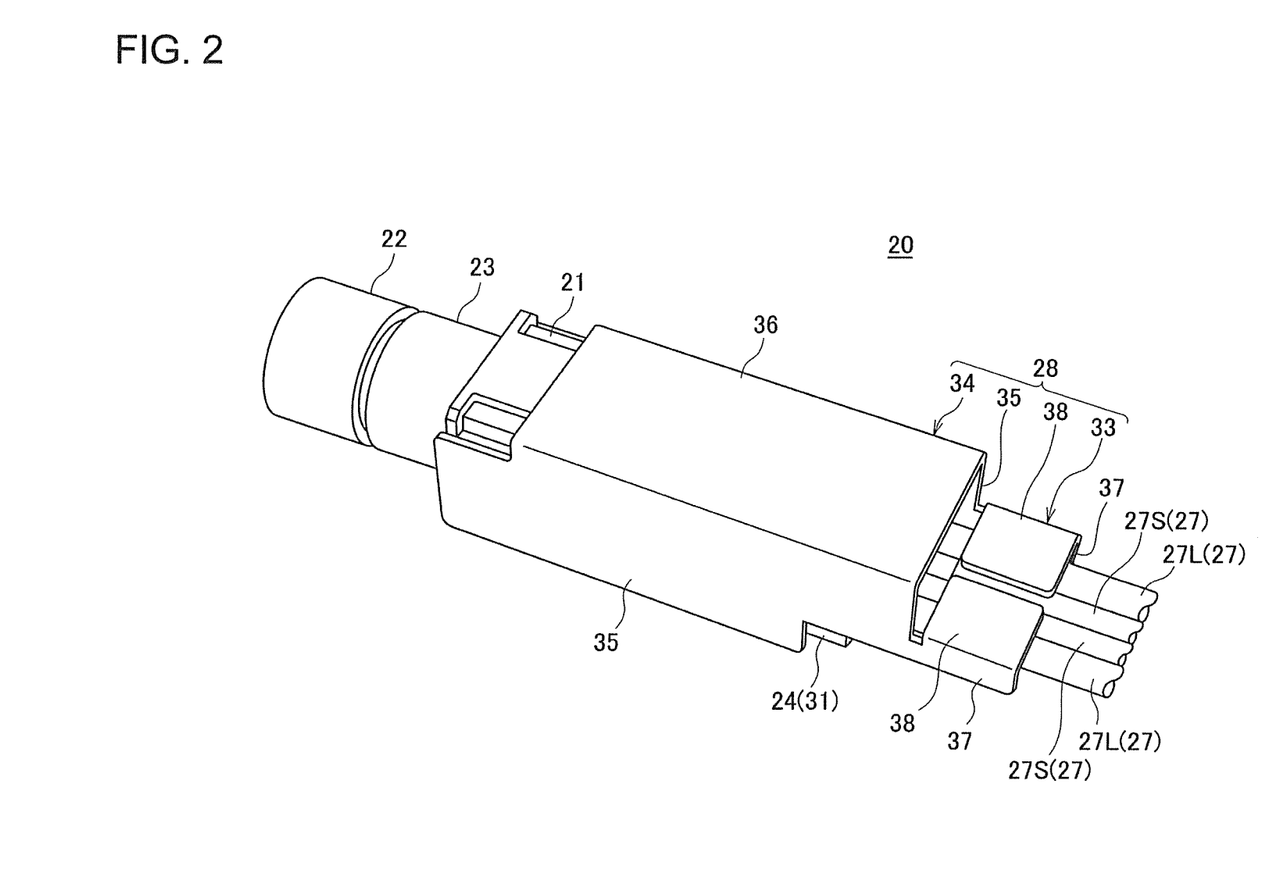
FIG. 2 is a perspective view of an imaging unit that is installed in a tip portion of an insertion unit of an endoscope shown in FIG. 1.

The case member 28 has a holding portion 33 which hold the plural cables 27 and a cover portion 34 which covers part of the image sensor 21 and part of the circuit board 24. The cover portion 34 is composed of a pair of side walls 35 and a ceiling wall 36 which connects the pair of side walls 35.

The pair of side walls 35 extend alongside a pair of side surfaces, extending perpendicularly to the photodetecting surface 21a of the image sensor 21, of the circuit board 24, respectively. The ceiling wall 36 covers the board surface, formed with the lands 32, of the cable connection portion 31 of the circuit board 24 and the terminal portions, connected to the respective lands 32, of the cables 27.

The holding portion 33 has a pair of extension side walls 37 that are connected to the pair of side walls 35 of the cover portion 34, respectively. The pair of extension side walls 37 project rearward from the cover portion 34 perpendicularly to the photodetecting surface 21a of the image sensor 21 and are located on the two respective sides, in the arrangement direction of the plural cables 27, of the cables 27 which are arranged in a plane that is parallel with the board surface of the cable connection portion 31 of the circuit board 24.

Presser pieces 38 project from the top edges of the pair of extension side walls 37, respectively, and are placed on the plural cables 27 interposed between the pair of extension side walls 37 from the side opposite to the board surface of the cable connection portion 31. As a result, the plural cables 27 are kept arranged in the same plane even in the rear of the cable connection portion 31 as over the board surface of the cable connection portion 31.

The presser pieces 38 which are placed on the plural cables 27 are located closer to the side of the cable connection portion 31 than the ceiling wall 36 of the cover portion 34 is, and a step is thereby formed between the ceiling wall 36 and the presser pieces 38.

Figure 6:
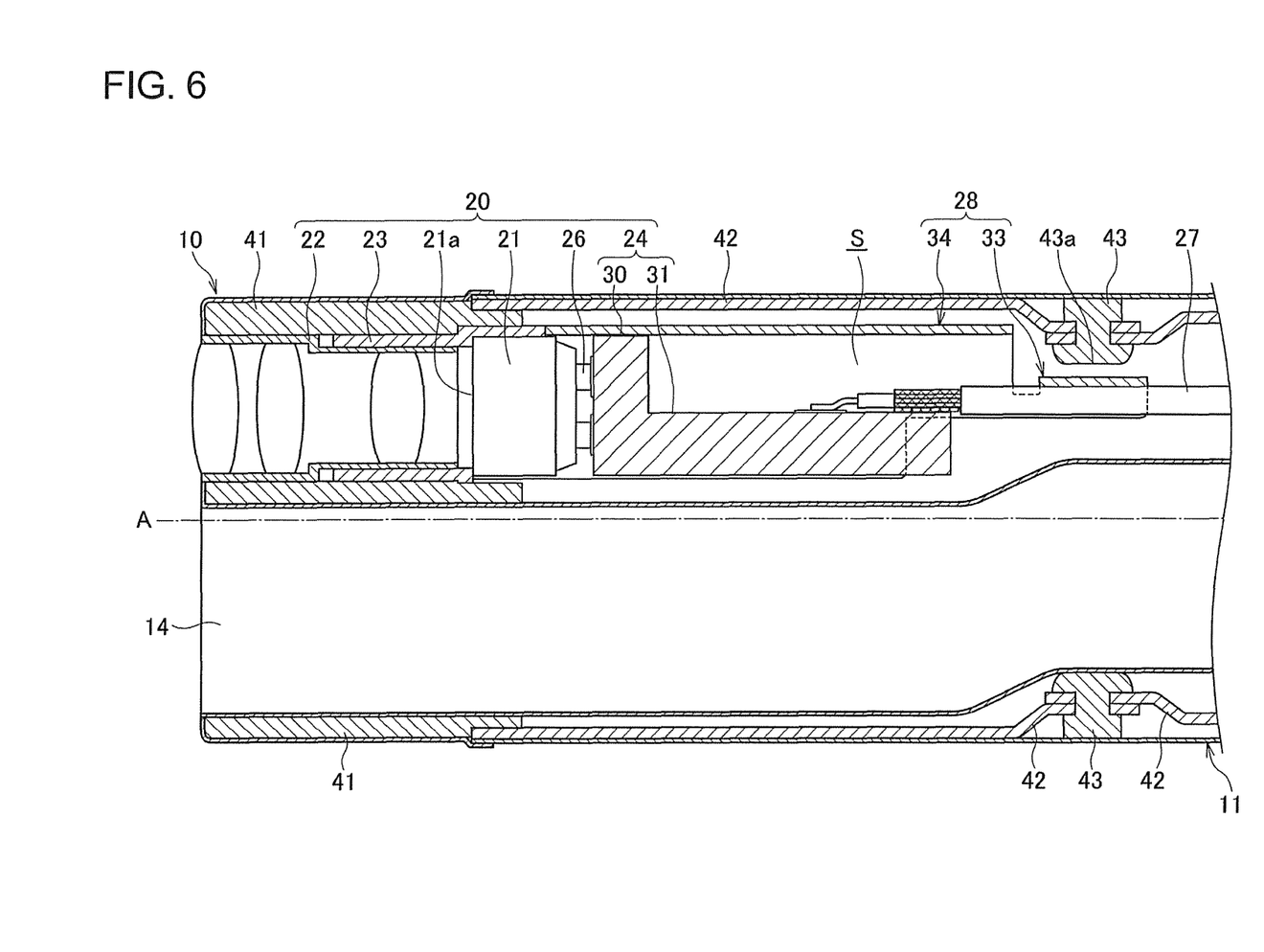
FIG. 6 is a longitudinal sectional view of the tip portion and a bendable portion of the insertion unit of the endoscope shown in FIG. 1.
Figure 7:
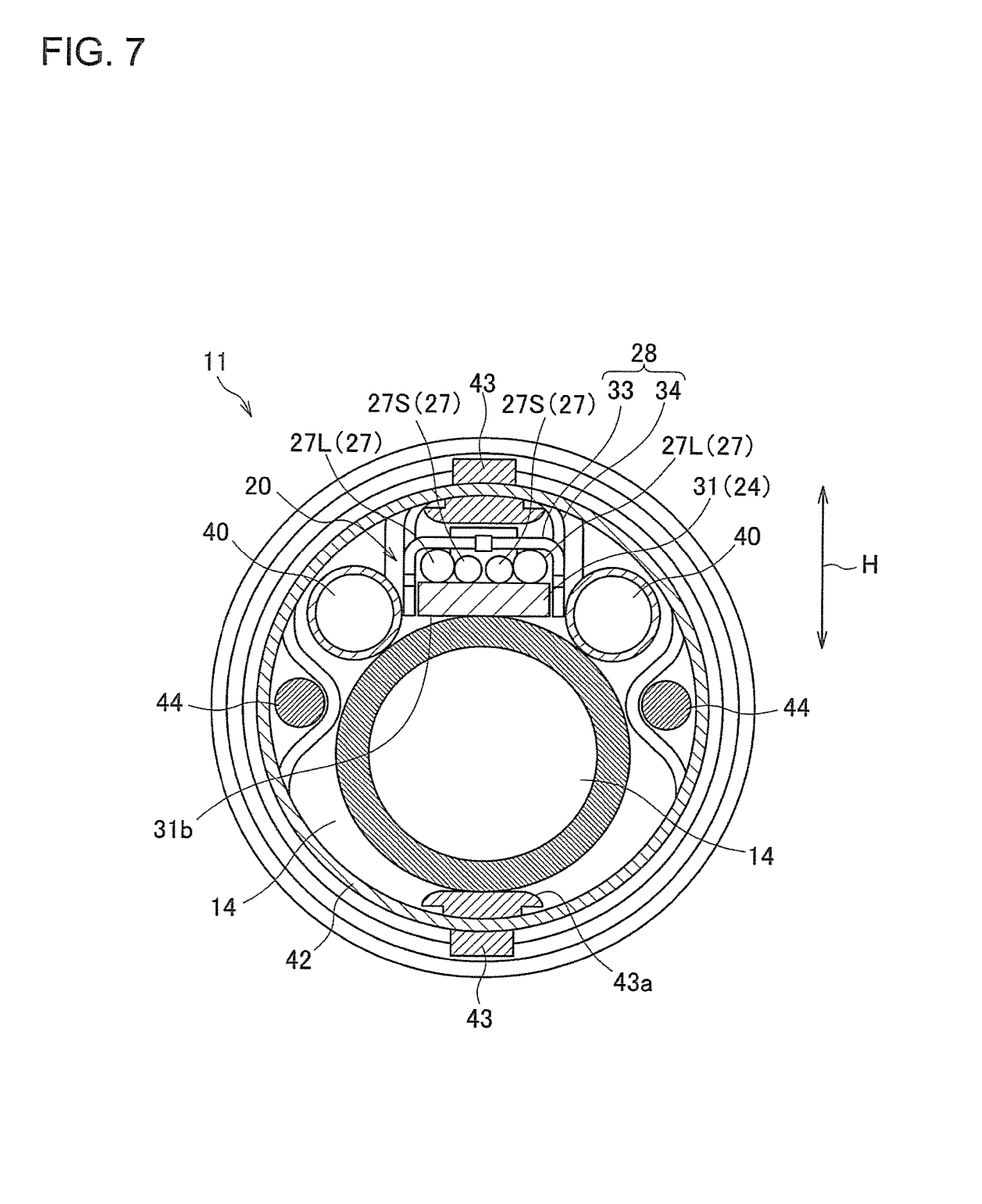
FIG. 7 is a transverse sectional view of the bendable portion of the insertion unit of the endoscope shown in FIG. 1.

FIGS. 6 and 7 illustrate the structures of the tip portion 10 in which the imaging unit 20 is installed and the bendable portion 11 of the insertion unit 6.

The above-described imaging unit 20, a tip portion of the treatment tool channel 14, the illumination optical systems for emitting illumination light guided from the light source unit 3 by the light guides 40, and other members are disposed in the tip portion 10. In the embodiment, the imaging unit 20 is disposed so that an outer surface 31b, opposite to the inner surface 31a, of the cable connection portion 31 of the circuit board 24 is adjacent to the side surface of the treatment tool channel 14.

The sensor holder 23 which holds the image sensor 21 and the lens barrel 22 is disposed in a housing hole of a tip hard portion 41 which is made of a metal material such as stainless steel, and is fixed to the tip hard portion 41. The tip portion of the treatment tool channel 14 and the illumination optical systems are also disposed in the housing hole of the tip hard portion 41 and are fixed to the tip hard portion 41.

The photodetecting surface 21a of the image sensor 21 which is held by the sensor holder 23 fixed to the tip hard portion 41 is oriented approximately perpendicularly to the longitudinal axis A of the insertion unit 6. The cable connection portion 31 which is approximately perpendicular to the photodetecting surface 21a extends parallel with the longitudinal axis A.

The bendable portion 11 includes plural ring-shaped joining pieces 42 which are arranged parallel with the longitudinal axis A, and is thereby formed as a tubular body that houses the plural cables 27 connected to the circuit board 24 of the imaging unit 20, the treatment tool channel 14, the light guides 40, etc.

Two adjoining joining pieces 42 are connected to each other by a pair of pins 43 disposed on an axial line that is approximately perpendicular to the longitudinal axis A, so as to be swingable about the axial line. The bendable portion 11 is bent as a whole as a result of combination of individual swings of pairs of adjoining joining pieces 42.

The bendable portion 11 is manipulated by the manipulation unit 7 via a pair of wires 44 which are inserted through the bendable portion 11 past the soft portion 12. When manipulated by the manipulation unit 7, one of the pair of wires 44 is pulled and the other is paid out, whereby the bendable portion 11 is bent.

Among the plural joining pieces 42 constituting the bendable portion 11, the head joining piece 42 located in the tip portion 10 is joined to the tip hard portion 41, whereby the tip portion 10 and the bendable portion 11 are connected to each other. In the tip portion 10 of the insertion unit 6, the circuit board 24 and the case member 28 (attached to the circuit board 24) of the imaging unit 20 whose sensor holder 23 is fixed to the tip hard portion 41 are disposed inside the head joining piece 42.

Heads 43a of the pair of pins 43 that connect the head joining piece 42 and the joining piece 42 adjacent to it project inward in the radial direction. A narrower space is formed at the position of this pair of pins 43 so as to be perpendicular to the axial direction of the insertion unit 6 and to be narrower in the radial direction than the portions, distant from the pair of pins 43 in the axial direction, of the two joining pieces 42 connected by the pair of pins 43.

The holding portion 33 of the case member 28 which is disposed inside the head joining piece 42 is located between the pair of pins 43, that is, in the narrower space formed inside the insertion unit 6, and holds, between the pair of pins 43, the plural cables 27 which are connected to the cable connection portion 31 of the circuit board 24.

As described above, the imaging unit 20 according to the embodiment is equipped with the circuit board 24 which is L-shaped when viewed in the width direction (indicated by arrow W in FIG. 3) that is perpendicular to the longitudinal direction of the insertion unit 6. And one (first leg), located behind the image sensor 21, of the two orthogonal legs constituting the circuit board 24 is the sensor connection portion 30 and the other (second leg), extending perpendicularly to the photodetecting surface 21a of the image sensor 21, is the cable connection portion 31. The connection terminals 26 of the image sensor 21 are connected to the respective lands 25 of the connection surface 30a of the sensor connection portion 30, and the transmission cables, that is, the four cables 27, are electrically connected to the lands 32 of the inner surface 31a of the cable connection portion 31.

Since as described above the plural cables 27 which are inserted through the insertion unit 6 are connected, in a concentrated manner, to the one surface (inner surface 31a of the cable connection portion 31) of the circuit board 24 to which the connection terminals 26 of the image sensor 21 are connected, the process of connecting the plural cables 27 to the circuit board 24 is much simpler than corresponding conventional processes, which makes it easy to manufacture the imaging unit 20.

Incorporating this imaging unit 20, the endoscope 2 is also easy to manufacture and can be reduced in the width of the insertion unit 6. In particular, although in the embodiment the outer size of the image sensor 21 is smaller than or equal to a 1-mm square and hence the imaging unit 20 is required to be high in dimensional accuracy, the imaging unit 20 can be miniaturized with high accuracy because as described above the process of connecting the plural cables 27 to the circuit board 24 is much simpler than corresponding conventional processes.

As described above, in the embodiment, the circuit board 24 is disposed so as to be completely hidden behind the image sensor 21 when viewed from the side of the photodetecting surface 21a of the image sensor 21 in the direction of the optical axis B, that is, so that the projection area, projected in the direction of the optical axis B, of the former is completely contained in that of the latter. With this measure, as seen from FIGS. 8A and 8B, even if the cable connection portion (second leg) 31 which is the longer leg of the circuit board 24 is warped, elongation of the imaging unit 20 in the warp direction can be prevented.

Figure 8A:
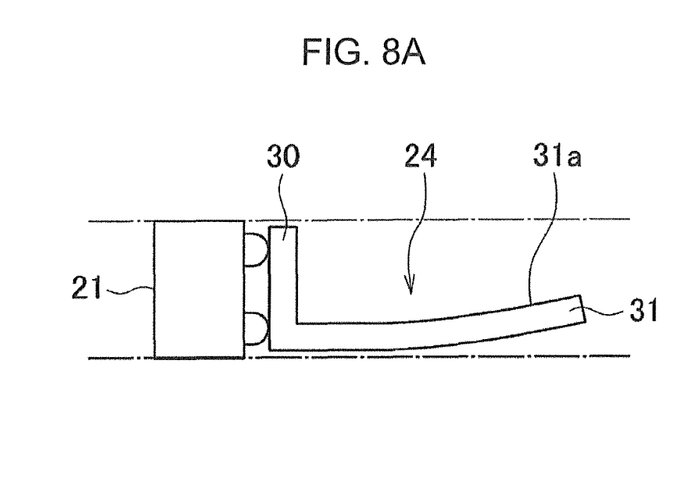
Figure 8B:
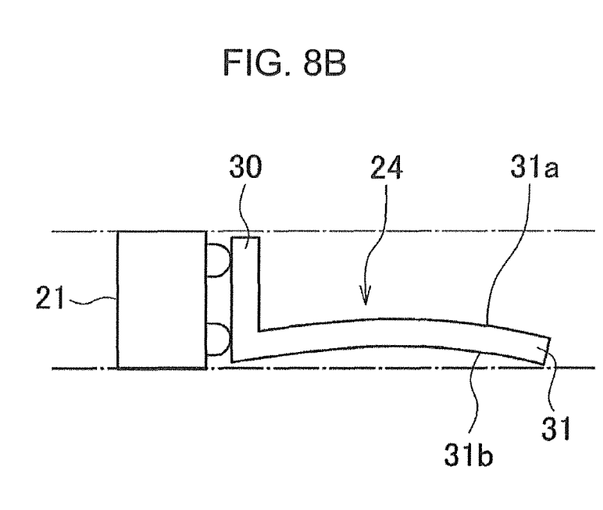

For example, when the cable connection portion 31 is warped to the side of its inner surface 31a, as shown in FIG. 8A the circuit board 24 is disposed so that the outermost edge of the projection area of the cable connection portion 31 coincides with that of the image sensor 21. Also when the cable connection portion 31 is warped to the side of its outer surface 31b, as shown in FIG. 8B the circuit board 24 is disposed so that the outermost edge of the projection area of the cable connection portion 31 coincides with that of the image sensor 21. Thus, dimensional increase of the imaging unit 20 can be avoided by disposing the circuit board 24 so that it does not stick out of the area that is hidden behind the image sensor 21 by adjusting the angular relationship between the image sensor 21 and the circuit board 24.

Furthermore, since the circuit board 24 is L-shaped, even with a warped cable connection portion 31, a sufficiently large space for arrangement of the plural cables 27 can be secured between the inner surface 31a of the cable connection portion 31 and the outer periphery of the projection area of the image sensor 21 in the area that is hidden behind the image sensor 21.

As described above, in the embodiment, since the imaging unit 20 is disposed so that the outer surface 31b of the cable connection portion 31 is adjacent to the side surface of the treatment tool channel 14 (see FIG. 7), the insertion unit 6 of the endoscope 2 can be narrowed most effectively. Whereas the dimension of the imaging unit 20 in its width direction (indicated by arrow W in FIG. 3) tends to vary being affected by the connection accuracy of the plural cables 27 and other factors, the dimension of the imaging unit 20 in such a direction (indicated by arrow H in FIGS. 4 and 7) as to be affected only by the molding accuracy of the circuit board 24 is less prone to vary. Thus, the total length of imaging unit 20 and the treatment tool channel 14 in the radial direction of the insertion unit 6 can be reduced effectively by disposing the imaging unit 20 so that the outer surface 31b of the cable connection portion 31 is adjacent to the side surface of the treatment tool channel 14. The insertion unit 6 of the endoscope 2 can thus be narrowed effectively.

It is noted that the same effect can be obtained by disposing the imaging unit 20 so that the inner surface 31a of the cable connection portion 31 is adjacent to the side surface of the treatment tool channel 14.

As described above, in the embodiment, the transmission cables which are the four cables 27, that is, the two first cables 27L which are relatively large in diameter and the two second cables 27S which are relatively small in diameter, are electrically connected to the cable connection portion 31 and the first cables 27L are disposed as the outermost cables in the width direction (indicated by arrow W in FIG. 3). Since the two relatively wide first cables 27L are disposed outside and the two relatively narrow second cables 27S are disposed inside them, the width of the cable connection portion 31 (i.e., its dimension in the direction indicated by arrow W in FIG. 3) can be minimized while the width of the lands 32, the interval between adjoining lands 32, and the interval between the outermost lands 32 and the edges of the cable connection portion 31 of the circuit board 24 are kept sufficiently large.

Figure 9A:
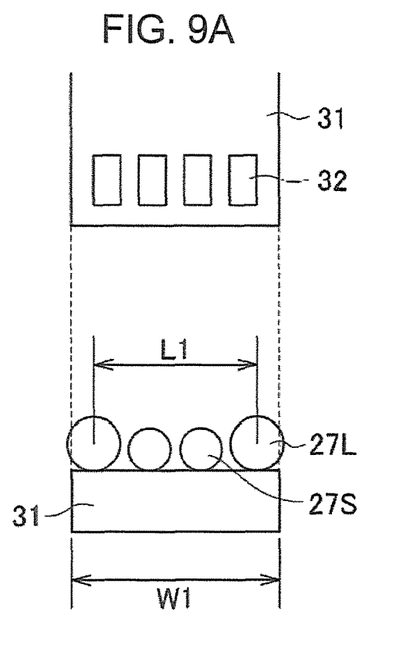
Figure 9B:
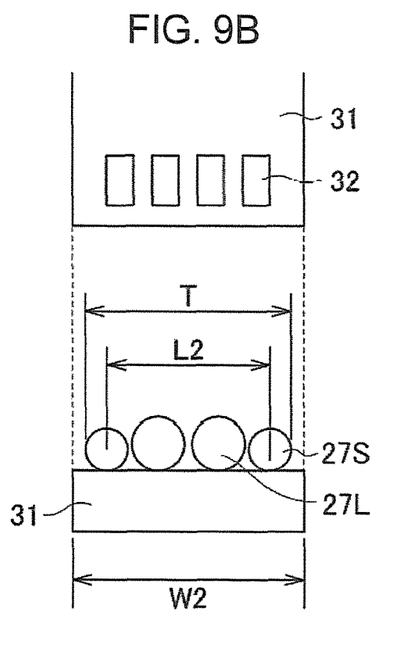

Referring to FIGS. 9A and 9B, a description will now be made of why the necessary width of the cable connection portion 31 varies between the case that the first cables 27L are disposed outside the second cables 27S and the case that the former are disposed inside the latter. The gap between adjoining cables 27 are represented by s and the diameters of each first cable 27L and each second cable 27S are represented by D and d, respectively. These parameters have a relationship $s<d<D$.

As shown in FIG. 9A, in the case where the relatively wide first cables 27L are disposed outside, the interval L1 between the centers of the two first cables is calculated as $L1=2d+3S+D/2\times2$. On the other hand, as shown in FIG. 9B, in the case where the relatively narrow second cables 27S are disposed outside, the interval L2 between the centers of the two second cables 27S is calculated as $L2=2d+3S+d/2\times2$. The center-to-center distance L1 of the former case is shorter than the center-to-center distance L2 of the latter case by $D-d$ (i.e., $L1<L2$). Thus, under the condition that the width of the lands 32 and the interval (clearance) between adjoining lands 32 are kept the same, the necessary width W1 of the cable connection portion 31 in the case where the first cables 27L are disposed outside (FIG. 9A) is shorter than the necessary width W2 of the cable connection portion 31 in the case where the second cables 21S are disposed outside (FIG. 9B).

If the area of each land 32 and the gap area between adjoining lands 32 are increased, the necessary width W2 in the case where the second cables 27S are disposed outside becomes greater than the total length T including the gaps between the four cables 27 ($T<W2$).

Considering the above, in the embodiment, the relatively wide first cables 27L are disposed outside as shown in FIG. 9A. Even if the difference between the necessary widths W1 and W2 is as short as about 0.1 mm, this difference is very significant in developing the endoscope 2 which incorporates the image sensor 21 having an outer size smaller than or equal to a 1-mm square and hence is required to decreased in width on the order of 0.1 mm or less.

As described above, in the embodiment, the relatively wide first cables 27L are used as cables for transmitting signals that likely cause problems if distorted in waveform, such as a clock signal cable and an output signal cable. On the other hand, the relatively narrow cables 27S are used as cables for which parameter adjustment is possible, such as a power cable and a ground cable. Where plural cables having different diameters are used in mixture in this manner, the necessary width of the cable connection portion 31 can be made smaller than in the case that cables having the same diameter are used.

As described above, in the embodiment, the shield conductors 27b of the first cables 27L which are close to the metal (conductor) case member 28 are electrically connected to it. In this manner, a measure against electrostatic breakdown can be taken utilizing the case member 28 effectively.

Figure 10:
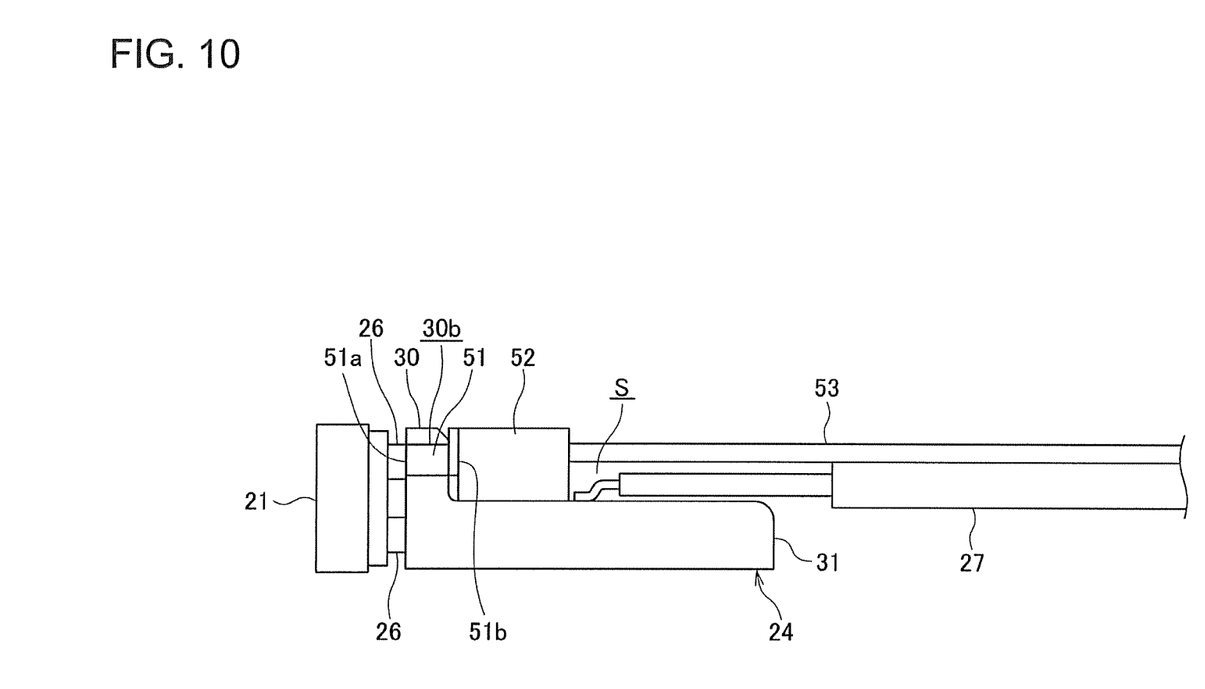
FIG. 10 is a sectional view of an imaging unit which is a modification of the imaging unit according to the embodiment.

FIG. 10 shows a modification of the imaging unit 20 according to the embodiment. In the imaging unit shown in FIG. 10, the sensor connection portion (first leg) 30 of the circuit board 24 has a through-hole(s) 30b which penetrates through the sensor connection portion 30 from its connection surface 30a to a space S adjacent to the inner surface 31a of the cable connection portion (second leg) 31. Heat transfer members 51 which are penetration electric wires are inserted in the through-hole (s) 30b, and heat radiation members 52 are disposed in the space S so as to be fixed to the inner surface 31a of the cable connection portion 31. The heat radiation members 52 are in contact of the case member 28. One ends 51a of the heat transfer members 51 are connected to the corresponding connection terminals 26 of the image sensor 21 via the lands 25 or the like formed on the connection surface 30a, respectively, and the other ends 51b are connected to the respective heat radiation members 52. Heat radiation wires 53 which extend parallel with the first cables 27L and the second cables 27S are connected to the end surfaces, opposite to the heat transfer members 51, of the heat radiation members 52, respectively.

Since the heat transfer members 51 and the heat radiation members 52 are provided in or on the circuit board 24 and the heat radiation wires 53 are connected to the heat radiation members 52, heat generated by the image sensor 21 is allowed to escape to the case member 28 and the heat radiation wires 53 via the heat transfer members 51 and the heat radiation members 52. Thus, a heat radiation path that is sufficiently large in heat capacity can be realized.

In the above-explained embodiment, each of the heat transfer members 51, the heat radiation members 52 and the heat radiation wires 53 are described as plural form, but it is possible that each of those three kinds of members is constituted by a single member.

As explained above, according to an aspect of the invention, there is provided an endoscope having an imaging unit at a tip portion of an insertion unit to be inserted into a body cavity, the imaging unit comprising: a solid-state imaging device which is disposed in such a manner that its photodetecting surface crosses the longitudinal direction of the insertion unit and which performs photoelectric conversion on an optical image formed on the photodetecting surface; a circuit board having a connection surface which is opposed to a surface, opposite to the photodetecting surface and formed with connection terminals, of the solid-state imaging device and which serves for electrical connection to the connection terminals of the solid-state imaging device, wherein: the circuit board is a rigid board that is L-shaped when viewed in its width direction that is perpendicular to the longitudinal direction of the insertion unit; and of a first leg and a second leg that constitute the L-shaped circuit board and are perpendicular to each other, the first leg which is opposed to the solid-state imaging device has the connection surface on the side of the solid-state imaging device and transmission cables are electrically connected to an inner surface of the second leg, the inner surface having a smaller area, than an area of an outer surface of the second leg, in a plane including the longitudinal direction of the insertion unit and the width direction of the circuit board, the outer surface being opposite to the inner surface.

It is preferable that the circuit board is disposed so that an outermost edge of the circuit board coincides with an outermost edge of the solid-state imaging device when the circuit board and the solid-state imaging device are projected onto a plane that is perpendicular to the longitudinal direction of the insertion unit.

It is preferable that the endoscope further comprises a treatment tool channel which is disposed parallel with the longitudinal direction of the imaging unit in such a manner that the inner surface or the outer surface, opposite to the inner surface, of the second leg of the circuit board is adjacent to a side surface of the treatment tool channel when viewed in the longitudinal direction of the insertion unit.

It is preferable that the first leg of the circuit board has a through-hole which penetrates through the first leg from its connection surface to a space adjacent to the inner surface of the second leg; and the endoscope further comprises: a heat transfer member provided in the through-hole; and a heat radiation member which is disposed in the space and connected to the heat transfer member.

It is preferable that the heat transfer member is an electric wire.

It is preferable that the transmission cables have four or more cables including a first cable having a relatively large diameter and a second cable having a relatively small diameter; the four or more cables are arranged on the inner surface of the second leg of the circuit board in its width direction; and the first cable is located at an outermost position in the width direction.

It is preferable that the first cable is a coaxial cable in which a center conductor is shielded by a shield conductor that surrounds the center conductor; and the shield conductor is electrically connected to a conductive cover member that covers the transmission cables partially.

It is preferable that a clock signal cable and an output signal cable are provided as first cables.

It is preferable that the connection surface of the circuit board is directly connected to the connection terminals of the solid-state imaging device.

It is preferable that an outer size of the solid-state imaging device is smaller than or equal to a 1-mm square when viewed perpendicularly to the photodetecting surface of the solid-state imaging device.

What is claimed is:

1. An endoscope having an imaging unit at a tip portion of an insertion unit to be inserted into a body cavity, the imaging unit comprising:
    a solid-state imaging device which is disposed in such a manner that a photodetecting surface thereof crosses a longitudinal direction of the insertion unit and which performs photoelectric conversion on an optical image formed on the photodetecting surface;

a circuit board having a connection surface which is opposed to a surface, opposite to the photodetecting surface and formed with connection terminals, of the solid-state imaging device and which serves for electrical connection to the connection terminals of the solid-state imaging device, wherein:

the circuit board is a rigid board that is L-shaped when viewed in a width direction of the circuit board that is perpendicular to the longitudinal direction of the insertion unit; and of a first leg and a second leg that constitute the L-shaped circuit board and are perpendicular to each other, the first leg which is opposed to the solid-state imaging device has the connection surface on the side of the solid-state imaging device and transmission cables are electrically connected to an inner surface of the second leg, the inner surface having a smaller area, than an area of an outer surface of the second leg, in a plane including the longitudinal direction of the insertion unit and the width direction of the circuit board, the outer surface being opposite to the inner surface, wherein the transmission cables have four or more cables including a first cable and a second cable;

a diameter of the first cable is greater than a diameter of the second cable;

the four or more cables are arranged on the inner surface of the second leg of the circuit board in the width direction of the circuit board; and the first cable is located at an outermost position in the width direction of the circuit board, wherein an outer size of the solid-state imaging device is smaller than or equal to a 1-mm square when viewed perpendicularly to the photodetecting surface of the solid-state imaging device, wherein the first leg of the circuit board has a through-hole which penetrates through the first leg from the connection surface of the first leg to a space adjacent to the inner surface of the second leg; and the endoscope further comprises:
  a heat transfer member provided in the through-hole; and
  a heat radiation member which is disposed in the space and connected to the heat transfer member.

2. The endoscope according to claim 1, wherein the circuit board is disposed so that an outermost edge of the circuit board coincides with an outermost edge of the solid-state imaging device when the circuit board and the solid-state imaging device are projected onto a plane that is perpendicular to the longitudinal direction of the insertion unit.

3. The endoscope according to claim 1, further comprising a treatment tool channel which is disposed parallel with the longitudinal direction of the insertion unit in such a manner that the inner surface or the outer surface, opposite to the inner surface, of the second leg of the circuit board is adjacent to a side surface of the treatment tool channel when viewed in the longitudinal direction of the insertion unit.

4. The endoscope according to claim 2, further comprising a treatment tool channel which is disposed parallel with the longitudinal direction of the insertion unit in such a manner that the inner surface or the outer surface, opposite to the inner surface, of the second leg of the circuit board is adjacent to a side surface of the treatment tool channel when viewed in the longitudinal direction of the insertion unit.

5. The endoscope according to claim 1, wherein the heat transfer member is an electric wire.

6. The endoscope according to claim 1, wherein:
  the first cable is a coaxial cable in which a center conductor is shielded by a shield conductor that surrounds the center conductor; and
  the shield conductor is electrically connected to a conductive cover member that covers the transmission cables partially.

7. The endoscope according to claim 1, wherein a clock signal cable and an output signal cable are provided as first cables.

8. The endoscope according to claim 6, wherein a clock signal cable and an output signal cable are provided as first cables.

9. The endoscope according to claim 1, wherein the connection surface of the circuit board is directly connected to the connection terminals of the solid-state imaging device.

10. The endoscope according to claim 2, wherein the connection surface of the circuit board is directly connected to the connection terminals of the solid-state imaging device.

* * * * *